United States Patent
Jonbrink

(10) Patent No.: US 6,520,944 B1
(45) Date of Patent: Feb. 18, 2003

(54) DIAPER THAT INCLUDES EXCREMENT ENCAPSULATING MEANS

(75) Inventor: Anna Karin Jonbrink, Lerum (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/333,990

(22) Filed: Jun. 16, 1999

(30) Foreign Application Priority Data

Jun. 17, 1998 (SE) ................................. 9802167

(51) Int. Cl.[7] ................................. A61F 13/20
(52) U.S. Cl. ..................... 604/385.13; 604/385.01; 604/385.11; 604/395
(58) Field of Search ................ 604/383, 385.01, 604/385.11, 385.13, 385.201, 385.27, 395, 385.18

(56) References Cited

U.S. PATENT DOCUMENTS 4,772,282 A * 9/1988 Oakley ................ 604/385.1
5,624,420 A * 4/1997 Bridges et al. ............. 604/365
5,807,371 A * 9/1998 Toyoda et al. ............ 604/385.1
5,989,236 A * 11/1999 Roe et al. ................ 604/385.1
6,110,157 A * 8/2000 Schmidt ................ 604/385.01

* cited by examiner

*Primary Examiner*—John G. Weiss
*Assistant Examiner*—Michele Kidwell
(74) *Attorney, Agent, or Firm*—Young & Thompson

(57) ABSTRACT

A diaper has a front part, a rear part and an intermediate crotch part which includes an absorbent body that extends in the longitudinal direction of the diaper from the rear part, through the crotch part and into the front part and which is spaced from the end-edge of the rear part and/or the front part. A weakening line is provided transversely in that part of the diaper which lies longitudinally outside the absorbent body, in the front or the rear part. The weakening line terminates at a distance from the side-edges of the diaper in the diaper part.

9 Claims, 2 Drawing Sheets

DIAPER THAT INCLUDES EXCREMENT ENCAPSULATING MEANS

FIELD OF INVENTION

The present invention relates to a diaper that has a front part, a rear part and an intermediate crotch part and an absorbent body or pad which extends in the longitudinal direction of the diaper from the rear part thereof, through the crotch part and into the front part and which is spaced from the end-edge of said rear part and/or said front part.

BACKGROUND OF THE INVENTION

It is not always possible to immediately discard used and dirty diapers, which makes it necessary to keep the diapers about one's person in certain cases, e.g. on a baby carriage or perambulator, until a convenient place for discarding the diapers can be found. Consequently, in order to enable such diapers to be handled hygienically, it is desirable that the diapers can be sealed after use.

This problem has been solved traditionally, by also using the diaper fastener tabs to close and seal a dirty diaper. One drawback with this solution is that the adhesive strength of such tabs, or tapes, of a used diaper is often insufficient to securely seal the diaper, due to the presence of baby powder, some other type of powder, or because parts of the outer sheet of the diaper have fastened to the adhesive coating of the tape and therewith impaired its adhesive strength.

One problem solution to the same end is to utilize the mechanical fastener elements with which diapers are now often provided. Examples of such solutions are given in EP-A1 -01 321 234 and EP-B1-0 374 730. One drawback with these solutions is that it is necessary to provide the diaper with separate elements that can coact with these mechanical fastener elements, which naturally makes manufacture more difficult and more expensive. Another problem is that positioning of the fastener elements is a sensitive matter, since the fastener tabs that carry the mechanical fastener elements have a limited span.

Another solution is to provide the diaper with an extra sheet of material at one end of the rear side thereof, this sheet being turned over to the other side of the diaper so as to form a pocket in which the dirty diaper can be kept when rolled-up. Examples of such a solution are disclosed in U.S. Pat. No. 5,071,414 and SE-B-456 311. This solution makes manufacture of the diaper more difficult and more expensive.

There is therefore a need of designing diapers that can be sealed after use regardless of the design of the fastener elements, without needing additional sheets or components and without making the manufacturing process more difficult to any appreciable extent.

SUMMARY OF THE INVENTION

According to the present invention, the aforesaid requirements are met with a diaper that has a front part, a rear part and an intermediate crotch part and which includes an absorbent body or pad that extends in the longitudinal direction of the diaper from its rear part and through the crotch part and into the front part of the diaper and which is spaced from the end-edge of the rear part and/or the front part, said diaper being characterised by a weakening line which extends transversely in that part of the diaper that lies longitudinally outside the absorbent body in the front or rear diaper part, said weakening line terminating short of the side edges of said diaper part. When a dirty diaper is removed and the diaper is torn along the weakening line, that part of the diaper that lies longitudinally outside the weakening line will form a loop which can be threaded over a rolled-up diaper so as to hold the diaper in its rolled-up state.

In one preferred embodiment of the invention, the weakening line terminates at the same distance from respective side edges of the diaper. The weakening line may comprise a row of perforations, a through-penetrating slot or a slit and the diaper includes waist elastic, wherein the weakening line extends within the region of this elastic and at least a part of said waist elastic is located closer to the end-edge of that diaper part in which the weakening line is provided than said weakening line. In one variant, the weakening line has a length that corresponds to the largest width of the absorbent body. In another variant, the end-edges of the absorbent body are spaced from the end-edges of the front part and the rear part of said diaper and a transverse weakening line extends between the end-edge of the diaper and the end-edge of the absorbent body in both the front and the rear diaper parts.

It will be understood that the term diaper as used here includes all types of diaper, such as conventional diapers and pants-like diapers, so-called trainers, and also incontinence protectors and like absorbent articles.

BRIEF DESCRIPTION OF THE DRAWINGS

The invention will now be described with reference to the accompanying drawings, in which.

DETAILED DESCRIPTION OF EXEMPLIFYING EMBODIMENTS OF THE INVENTION

Figure 1:
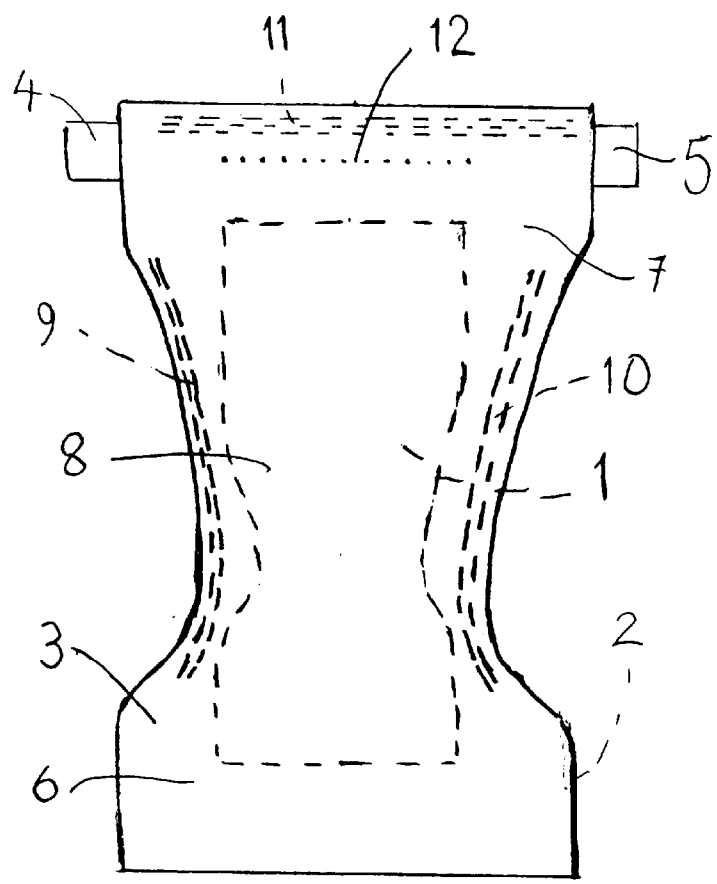
FIG. 1 illustrates schematically and from above a diaper according to a first embodiment of the invention.

The diaper shown in FIG. 1 includes an absorbent body or pad 1 enclosed between a liquid-impermeable backing sheet 2 which lies distal from the viewer of FIG. 1, and a liquid-permeable outer sheet 3. The sheets 2 and 3 extend beyond the absorbent body 1, both laterally and longitudinally, and are joined together at those parts which lie outside the absorbent body. Fastener tabs 4, 5 extend from the side edges of the rear diaper part 7. These fastener tabs 4, 5 are provided with adhesive coatings and function to connect the side parts of the front diaper part 6 with the side parts of the rear diaper part 7. Leg elastic 9, 10 extends from the front part 6, through the crotch part 8 and into the rear part 7. Waist elastic 11 is disposed along the end-edge of the rear diaper part 7, in the form of several elastic threads, an elastic ribbon or the like.

The absorbent body is comprised of one or more layers of absorbent material, for instance cellulose fluff pulp, with or without an admixture of superabsorbent particles. The material used may be any one of those absorbent materials used in diapers and like articles. The liquid-impermeable outer sheet, or backing sheet, is comprised suitably of plastic film optionally laminated with nonwoven material, and the liquid-permeable sheet is comprised of a hydrophobic or hydrophilic nonwoven material or a laminate of different nonwoven materials. All materials that are used as outer sheets in diapers and like articles can be used in an inventive diaper.

In accordance with the invention, a weakening line 12 is provided transversely in the rear diaper part 7, in that portion of the diaper that lies longitudinally outside the absorbent body 1, between the end-edge of said body and the waist elastic 11. The weakening line 12 is comprised of a line of perforations in the illustrated embodiment, although it may, of course, be formed in some other way, e.g. by removing material from the outer sheets 2, 3. A line of perforations is preferred, however, since it is easier to provide a perforated line in which the perforations will safely resist the forces to which the diaper is subjected in use and can be easily opened by hand. When the diaper is in use, the forces acting on the perforations in the longitudinal direction of the diaper are very slight and the presence of said perforations will not therefore impair the mechanical strength of the diaper to any appreciable extent in practice. The forces are, in fact, so small as to enable a slit or a slot to be used instead of a line of perforations.

The weakening line 12 is preferably located at least 10 mm outside the end-edge of the absorbent body.

Figure 2:
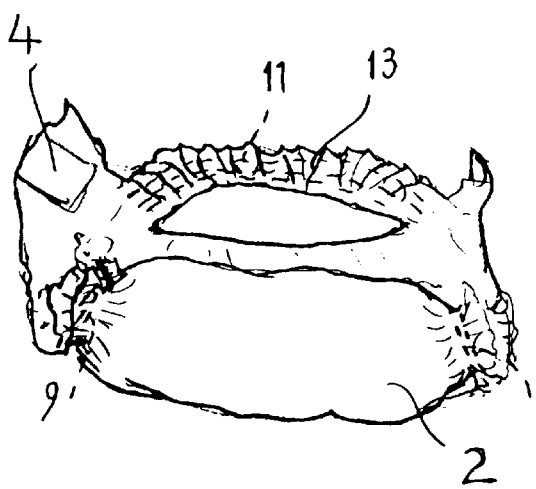
FIG. 2 illustrates the diaper of FIG. 1 in a rolled-up state.
Figure 3:
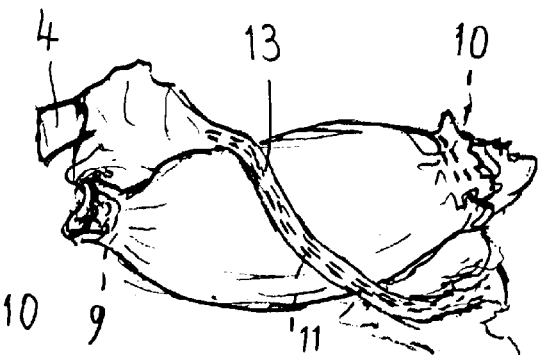
FIG. 3 illustrates the diaper of FIG. 2 in a sealed state.

When tearing along the perforations of a soiled diaper, the outermost portion of the rear diaper part will form an elongated elastic loop 13 whose ends are connected with the side-parts of the outer sheet of the rear diaper part 7. The soiled diaper is then rolled-up from the end of the front diaper part towards the rear diaper part, so as to encapsulate the liquid-permeable outer sheet 3 and the underlying absorbent body 1 in the liquid-impermeable sheet, therewith obtaining the configuration shown in FIG. 2. When the diaper has been rolled into this configuration, the loop 13 is drawn over the part of the diaper that has been rolled-up so as to obtain the configuration shown in FIG. 3, said diaper being held its rolled state through the medium of the loop 13. Thus, the invention enables a soiled napkin to be sealed in a simple and effective manner, solely as a result of the transversal perforated line 12.

In the illustrated embodiment, the fastener elements 4, 5 are comprised of adhesive tabs, although it will be understood that the invention can also be applied with diapers that have mechanical fastener elements. The weakening line may alternatively be provided in the front part of the diaper instead of its rear part, particularly if the front part is provided with waist elastic. It is also possible to provide weakening lines in both the front and the rear part of the diaper, so as to afford the user the greatest possible degree of freedom.

In order to ensure effective encapsulation of the contents of a soiled diaper, the length of the loop with the elastic contracted will preferably not be greater than the diameter of the rolled-up part of the diaper. Naturally, the diameter of the rolled-up part of the diaper will depend on how tightly said part has been rolled-up, among other things. It has been found in the case of the illustrated embodiment that the weakening line 12 will conveniently have a length that corresponds to the greatest width of the absorbent body in order to provide effective encapsulation, or sealing, of the waste contents of a diaper without needing to roll-up the diaper particularly tightly.

Figure 4:
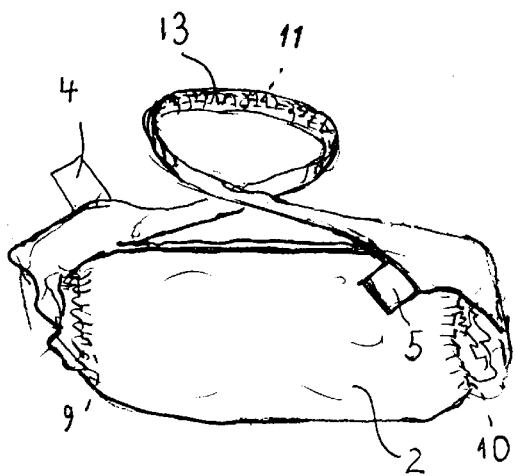
FIG. 4 is a view similar to the view of FIG. 2, with the loop twisted one-half turn about itself.

However, the loop may, of course, have a length which requires the diaper to be rolled-up very tightly in order to be able to thread the rolled-up part of the diaper through the loop. For this reason, the loop is conveniently given a size which enables it to be threaded over diapers that have been rolled-up relatively loosely. If the user feels that the loop is too long to satisfactorily seal the diaper, the effective length of the loop 13 can be shortened by twisting the loop one or more times around itself prior to threading the rolled-up diaper through the loop. FIG. 4 shows schematically the loop 13 twisted one-half turn around itself.

Because the absorbent body is deformable, the invention can also be applied with diapers that lack waist elastic. If the waist elastic is broad, the weakening line can be provided in that part of the front or rear diaper part that contains the waist elastic.

Figure 5:
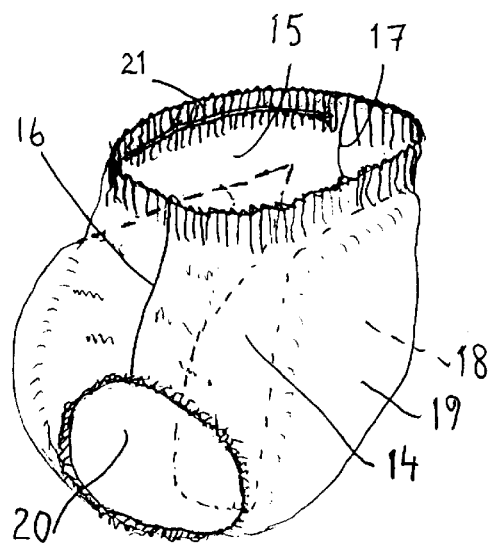
FIG. 5 is a perspective view of a pants-like diaper according to a second embodiment of the invention.

FIG. 5 illustrates schematically and in perspective a pants-type diaper according to a second embodiment of the invention. A pants-type diaper is put on and taken off in the same way as a pair of underpants and differs from a conventional diaper by virtue of the fact that opposing side-parts of the front and rear diaper parts 14 and 15 have already been joined together in manufacture, so that when removed from its packet the diaper will have a pants-like configuration with a waist opening and two leg openings. In the case of conventional diapers, the diaper obtains its pants-like configuration when the diaper is put onto the wearer and fastened around his/her waist. In the illustrated example, the side-parts of the pants-type diaper are joined together by side seams 16, 17, although other types of joins may be used. The side joins may be of the kind which can be pealed or torn away or may be of a releasable and re-fastenable type. The pants-type diaper illustrated in FIG. 5 have an absorbent body 18 enclosed between a liquid-impermeable outer sheet 19, which faces towards the viewer of FIG. 5, and a liquid-permeable outer sheet 20. The diaper also includes leg elastic and a relatively broad waist elastic. The elastic is indicated in FIG. 5 solely by the puckers caused in the outer sheets by the elastic. It will be seen from the Figure that the end-edges of the absorbent body 18 are spaced from the waist opening. In accordance with the invention, a weakening line in the form of a slit 21 is provided in the rear diaper part within the region of the waist elastic. There is thus formed a loop which can be used to seal a rolled-up or folded diaper in the same way as the loop 13 described with reference to FIGS. 2–4.

Figure 6:
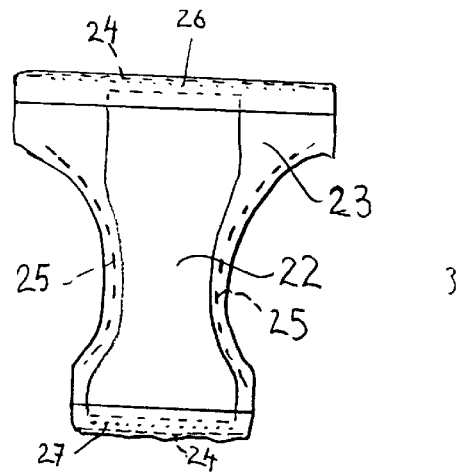
FIG. 6 illustrates from above a diaper blank which comprises a casing and an absorbent unit according to a third embodiment of the invention.

FIG. 6 illustrates a diaper blank according to a third embodiment of the invention. The diaper blank includes an absorption unit 22 consisting of an absorbent body that is enclosed between a liquid-permeable outer sheet, which faces towards the viewer of FIG. 6, and a liquid-impermeable outer sheet. The blank also includes an hour-glass casing 23 made of elastic material or material that has been made elastic. The casing has inwardly folded end-edges so as to form pockets for receiving the ends of the unit 22. The casing 23 also includes waist elastic 24 in the front and rear parts of the blank, and leg elastic 25. Lines of perforations 26, 27 are provided in the rear and front parts of the casing, in accordance with the present invention.

Fastener tabs or like fastener elements may be provided on the side parts of the casing 23, so as to enable a diaper to be formed from the blank. However, it is also conceivable to join the side-parts of the casing 23 together already in manufacture, so as to produce a pants-type diaper. In both cases, a user is able to tear along the perforations 27 in the front part or along the perforations 26 in the rear part and use the resultant loop to seal or encapsulate a soiled diaper or pants-type diaper in a manner analogous with that described with reference to FIGS. 2–4 with respect to the diaper of FIG. 1.

Figure 7:
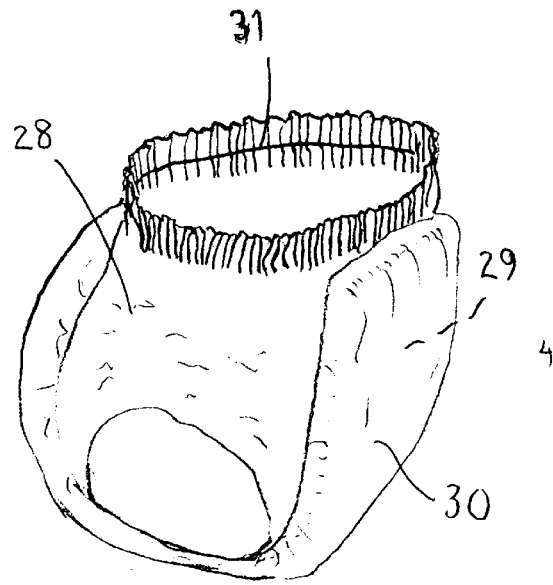
FIG. 7 is a perspective view of a pants-like diaper according to a fourth embodiment of the invention.

FIG. 7 illustrates a pants-type diaper having elastic inner pants 28 which support an absorbent body 29, and a liquid-impermeable outer sheet 30 which surrounds the outer side of the absorbent body. The outer sheet 30 is fastened to the outer side of the inner pants 28. According to the invention, a groove slit 31 is provided in the waist opening of the rear diaper part at a distance from the end-edge thereof. This groove slit will provide a looped part analogous with the loop 13 shown in FIGS. 2–4.

It will be understood that the illustrated embodiments can be modified within the scope of the invention, particularly with respect to the shape of the diaper and/or of the absorbent body, and the material from which the diaper is made. Furthermore, the different types of weakening lines illustrated in the various embodiments are exchangeable with one another. The weakening line need not necessarily be symmetrical relative to the symmetry axis of the diaper, but may well be located closer to one side-edge of the diaper than to its other side, naturally providing that the line will be sufficiently long to fulfil its purpose. The invention is therefore only restricted by the contents of the following claims.

What is claimed is:

1. A diaper comprising:
    a front part having an end-edge;
    a rear part having an end-edge;
    an intermediate crotch part, which includes an absorbent body that extends longitudinally in the diaper from the rear part, through the crotch part and into the front part, and which is spaced from the end-edge of at least one of said rear part and said front part; and
    a manually tearable weakening line extending transversely in a portion of the diaper which lies longitudinally outside the absorbent body in at least one of the front part and the rear part; said weakening line terminating short of side edges of the diaper in said portion;
    whereby an outermost portion of the diaper, which lies longitudinally outside the weakening line when torn, forms a loop structured and arranged to be threaded over the diaper, when the diaper is in a rolled-up state.

2. The diaper according to claim 1, wherein the weakening line terminates at the same distance from respective side edges of the diaper.

3. The diaper according to claim 1, wherein the weakening line is a line of perforations.

4. The diaper according to claim 1, wherein the weakening line is a through-penetrating slot or slit.

5. The diaper according to claim 1, wherein the diaper includes a waist elastic; the weakening line extends through a region of the waist elastic; and at least a part of the waist elastic is positioned between the end-edge of that part of the diaper and the weakening line.

6. The diaper according to claim 5, wherein the weakening line extends in the longitudinal direction of the diaper between an end-edge of the absorbent body and the waist elastic.

7. The diaper according to claim 1, wherein the weakening line has a length which corresponds to the greatest width of the absorbent body.

8. The diaper according to claim 1, wherein the absorbent body has opposite end-edges which are spaced from the end-edges of the front part and the rear part; and a weakening line extends transversely between the end-edge of the diaper and the end-edge of the absorbent body in both the front and the rear parts of the diaper.

9. The diaper according to claim 1, wherein the weakening line is spaced from the absorbent body at a distance of at least 10 mm in the longitudinal direction of the diaper.

* * * * *